(12) United States Patent
McInnes et al.

(10) Patent No.: US 10,183,093 B2
(45) Date of Patent: *Jan. 22, 2019

(54) WOUND DRESSING COMPOSITIONS

(71) Applicant: KCI USA, Inc., San Antonio, TX (US)

(72) Inventors: Rachael Louise McInnes, Skipton (GB); Breda Mary Cullen, Skipton (GB); Lindsay Page, Sutton-in-Craven (GB)

(73) Assignee: KCI USA, INC., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/458,845

(22) Filed: Aug. 13, 2014

(65) Prior Publication Data

US 2015/0030663 A1  Jan. 29, 2015

Related U.S. Application Data

(62) Division of application No. 12/516,487, filed as application No. PCT/GB2007/004201 on Nov. 2, 2007, now Pat. No. 8,834,905.

(30) Foreign Application Priority Data

Nov. 30, 2006 (GB) .................... 0623964.4

(51) Int. Cl.
| | |
|---|---|
| A61L 15/40 | (2006.01) |
| A61L 15/64 | (2006.01) |
| A61L 15/28 | (2006.01) |
| A61L 15/32 | (2006.01) |
| A61L 15/42 | (2006.01) |
| A61K 35/407 | (2015.01) |
| A61K 35/14 | (2015.01) |
| A61K 35/15 | (2015.01) |

(52) U.S. Cl.
CPC .............. *A61L 15/40* (2013.01); *A61K 35/15* (2013.01); *A61K 35/407* (2013.01); *A61L 15/28* (2013.01); *A61L 15/325* (2013.01); *A61L 15/425* (2013.01); *A61L 15/64* (2013.01)

(58) Field of Classification Search
CPC ....... A61K 35/15; A61K 35/407; A61L 15/40; A61L 15/325; A61L 15/64; A61L 15/28; A61L 15/425
See application file for complete search history.

(56) References Cited

U.S. PATENT DOCUMENTS

| | | | | |
|---|---|---|---|---|
| 5,324,508 | A * | 6/1994 | Adelstein | A61K 8/64 424/85.1 |
| 5,821,223 | A | 10/1998 | Rubin et al. | |
| 6,309,454 | B1 | 10/2001 | Harvey et al. | |
| 6,638,909 | B1 * | 10/2003 | Grady | A61K 38/57 424/445 |
| 7,264,826 | B2 | 9/2007 | Vervaet et al. | |
| 8,461,410 | B2 | 6/2013 | Cullen et al. | |
| 2005/0070494 | A1 * | 3/2005 | Cutroneo | C07H 21/00 514/44 A |
| 2005/0159695 | A1 | 7/2005 | Cullen et al. | |
| 2006/0039987 | A1 * | 2/2006 | Batycky et al. | 424/489 |
| 2006/0171930 | A1 | 8/2006 | Seyda et al. | |

FOREIGN PATENT DOCUMENTS

| | | | |
|---|---|---|---|
| EP | 0109089 A1 | | 5/1984 |
| EP | 1 758 637 B1 | | 2/2012 |
| GB | 2344519 | * | 6/2000 |
| GB | 2344519 A | | 6/2000 |
| GB | 2350565 A | | 12/2000 |

OTHER PUBLICATIONS

M. Huttunen et al. "Inhibition of Keratinocyte Growth in Cell Culture and Whole Skin Culture by Mast Cell Mediators". Experimental Dermatology, vol. 10, 2001, pp. 184-192.

* cited by examiner

*Primary Examiner* — Johann R Richter
*Assistant Examiner* — Genevieve S Alley
(74) *Attorney, Agent, or Firm* — Foley & Lardner LLP

(57) ABSTRACT

A wound dressing composition comprising a non-viable cell lysate or releasate derived from a hepatocyte cell or an inflammatory cell such as a macrophage. Also provided are wound dressings comprising such compositions, methods of making such compositions, and the use of such compositions for the treatment of wounds.

17 Claims, 3 Drawing Sheets

WOUND DRESSING COMPOSITIONS

Figure 1:
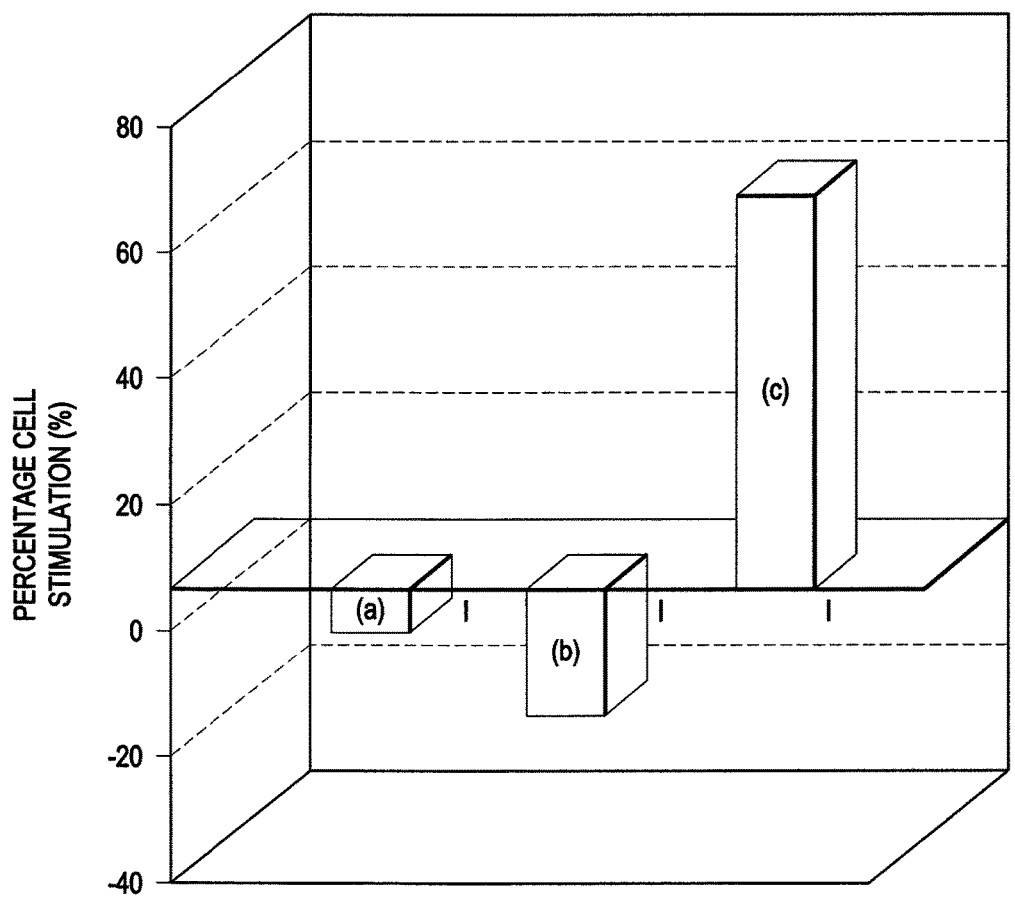

This application is a divisional of U.S. Non-Provisional patent application Ser. No. 12/516,487, filed Mar. 10, 2010, which claims the benefit of PCT/GB2007/004201, filed Nov. 2, 2007, which claims the benefit of GB 0623964.4, filed Nov. 30, 2006.

The present invention relates to wound dressing compositions comprising a non-viable cell lysate or releasate derived from macrophage or hepatocyte cells, to wound dressings comprising such compositions, to methods of manufacture of such compositions and dressings, and to the uses of the compositions and dressings for wound healing.

All documents mentioned in the text are incorporated herein by reference.

U.S. Pat. No. 6,585,969 describes the use of cultured keratinocyte sheets in wound healing. W0-A-2004050121 relates to a pharmaceutical composition comprising a non-viable keratinocyte cell lysate and an antisedimentation agent. The effectiveness of these wound dressings can be attributed to substances, such as growth factors, present in the cultured keratinocytes. Many known cytokines and growth factors, such as fibroblast growth factor (FGF), platelet derived growth factor (PDGF), epidermal growth factor (EGF), transforming growth factor alpha (TGF-alpha), transforming growth factor beta (TGF-beta) influence keratinocytes and skin fibroblasts. For example, TGF-beta, EGF and FGF induce keratinocyte proliferation. TGF-beta and PDGF stimulate the synthesis of collagen and other connective tissue components. Because of these properties, such growth factors may play a role in promoting wound healing and epidermal regeneration. Thus, the use of a cell culture or a cell releasate or lysate which contains such growth factors may be beneficial in promoting wound healing.

However, a problem with using such cell lysates to treat wounds is that wounds contain proteases, which can degrade the useful growth factors. The level of endogenous proteases is especially elevated in chronic wounds, such as ulcers. Therefore the full effect of such lysates is not achieved.

The present inventors have found that a macrophage or hepatocyte cell releasate/lysates promote fibroblast proliferation in vitro, even in the presence of chronic wound fluid. It is thought that this effect may be due to the presence in these lysates and releasates of protease inhibitors such as alpha-1-antitrypsin, in addition to growth factors. The effectiveness of these lysates and releasates as or in wound dressings is therefore expected to be greater than that of the keratinocyte dressings described above.

Accordingly, in a first aspect the present invention provides a wound dressing composition comprising a non-viable cell lysate or releasate derived from a hepatocyte cell or an inflammatory cell.

Inflammatory cells include macrophages, monocytes, lymphocytes, mast cells, neutrophils, T-cells, and plasma cells. Suitably, the inflammatory cell is a macrophage cell. Macrophages are cells that originate from specific white blood cells called monocytes. Macrophages mature from monocytes produced in the bone marrow. Monocytes and macrophages are phagocytes, acting in both non-specific defense as well as cell-mediated immunity of vertebrate animals.

Hepatocytes make up 60-80% of the cytoplasmic mass of the liver. The hepatocyte is the only cell in the body that manufactures albumin, fibrinogen and the prothrombin group of clotting factors. It is the main site for the synthesis of lipoproteins, transferrin, and glycoproteins. Hepatocytes manufacture their own structural proteins and intracellular enzymes.

The cell lysates and releasates used for the present invention may comprise components from cells other than macrophages or hepatocytes. However, preferably at least about 1%, more preferably at least about 10%, still more preferably at least about 30%, and most preferably about 50% or more of the cells used to prepare the lysate or releasate are macrophages and/or hepatocytes.

The term "cell lysate" refers to cell suspensions or fractions thereof, obtained by lysing the cells. The whole cell lysate contains all proteins and other molecules which were intended to remain intracellular and those intended to be secreted extracellularly. The cell lysates comprise an extremely complex mixture of constituents such as proteins, glycoproteins, polysaccharides, lipids, nucleic acids etc. All these components may interact with each other. The cell lysate in the solution or suspension of the present invention may comprise whole cells, parts of cells or any fractions or mixtures thereof obtained after a lysis step. The term "cell releasate" refers to those proteins and other molecules which are secreted extracellularly. Thus, the releasate can be regarded as a fraction of the lysate.

The cell lysate may be obtained from whole cells by any of the various cell lysis processes which are well known to those skilled in the art. The term "cell lysis" refers to rupturing the cell wall and/or the cell membrane of cells by a chemical, biological, mechanical or thermal treatment. Numerous mechanical methods of lysis have been developed and published. They include pressure, cavitation, sonic or ultrasonic waves, mechanical shaking or grinding. Cell lysates may suitably be obtained by mechanically homogenizing the cells.

The hepatocyte or macrophage cell lysates of the present invention may preferably be obtained by subjecting the cell suspension to multiple freeze-thaw cycles, which disrupt the cell membrane thereby releasing the cellular components into solution.

The whole cells may be primary isolates from human tissue, or the cells can be obtained from a culture collection such as the European tissue culture collection or the American Tissue Culture Collection. Once a vial of cells is bought/acquired they can be expanded and frozen stock maintained indefinitely using normal cell culture techniques.

Useful cell lysate fractions may be obtained by lysing whole cells, subjecting the resulting lysate to centrifugation wherein certain parts of the resulting cell lysate are in the pellet fraction and certain other parts of the resulting cell lysate are in the supernatant.

The cell lysate is suitably prepared by lysing a cellular composition, such as an aqueous cellular suspension, containing more than about $2 \times 10^5$ cells/ml, for example from $0.25 \times 10^6$ to about $5 \times 10^7$ cells/ml, preferably from about $0.5 \times 10^6$ to about $1 \times 10^7$ cells/ml. The concentration of the cell lysate in a composition of the present invention varies according to the type of cell lysate in the composition, as well as according to its intended use.

Releasates comprise proteins and other molecules, which the intact cell secretes during its normal growth cycle. Thus, the releasate is a sub-fraction of the cell lysate. The releasate is prepared by growing the cells in vitro and harvesting the conditioned media at different times, for example at 24 or 48 hours. The conditioned media contain the proteins, which the cells would normally secrete extracellularly in order to carry out their specific functions. Suitably, the cells are grown at a cell density of about 8×10⁶ cells/ml and releasates recovered after 24 hrs growth.

The cell releasates or lysates may be used directly, for example in aqueous suspension or in freeze-dried form. However, in most compositions according to the present invention the cell lysate or releasate is dispersed in or on a pharmaceutically acceptable vehicle. The vehicle maybe liquid, semi-solid (e.g. an ointment or a gel), or solid. Preferably, the compositions of the invention are suitable for topical application to a wound. Preferably, the compositions of the invention are substantially sterile.

The liquid or semi-solid vehicles may be any such vehicle suitable for supporting the cell lysate in the solution or suspension. Examples of such liquid vehicles are water, oil, or emulsions (such as water-in-oil or oil-in-water emulsions) and other similar liquids.

The solid compositions according to the present invention may be in the form of gels, beads, flakes, powder, and preferably in the form of a film, a fibrous pad, a web, a woven or non-woven fabric, a freeze-dried sponge, a foam, or combinations thereof. In certain embodiments, the material is selected from the group consisting of woven fabrics, knitted fabrics, and nonwoven fabrics, all of which may be made by conventional methods. In other embodiments, the material may comprise (or consist essentially of) a freeze-dried sponge or a solvent-dried sponge.

The solid vehicle maybe bioabsorbable or non-bioabsorbable. The term "bioabsorbable" refers to a material that is fully degraded and absorbed in vivo in the mammalian body.

Suitable non-bioabsorbable materials include common textile materials such as cellulose, processed cellulose such as viscose, polyamide, polyurethane, and also alginates.

Suitable bioabsorbable materials include those selected from the group consisting of collagens, bioabsorbable cellulose derivatives such as oxidized celluloses, galactomannans such as guar/borate, glycosaminoglycans such as cross-linked hyaluronates, chitosans, polylactides and polyglycolide polymers and copolymers, polyhydroxybutyrates, and mixtures thereof.

Preferably, the solid composition according to the present invention comprises, or consists essentially of, a bioabsorbable freeze-dried sponge. Suitable methods of making freeze-dried and solvent-dried sponges are described in EP-A-1153622 and EP-A-0838491.

In certain preferred embodiments the vehicle comprises (and may consist essentially of) a solid bioabsorbable material selected from the group consisting of collagens, chitosans, oxidized celluloses, and mixtures thereof.

Oxidized cellulose is produced by the oxidation of cellulose, for example with dinitrogen tetroxide. This process converts primary alcohol groups on the saccharide residues to carboxylic acid group, forming uronic acid residues within the cellulose chain. The oxidation does not proceed with complete selectivity, and as a result hydroxyl groups on carbons 2 and 3 are occasionally converted to the keto form. These ketone units introduce an alkali labile link, which at pH7 or higher initiates the decomposition of the polymer via formation of a lactone and sugar ring cleavage. As a result, oxidized cellulose is biodegradable and bioabsorbable under physiological conditions.

The preferred oxidized cellulose for practical applications is oxidized regenerated cellulose (ORC) prepared by oxidation of a regenerated cellulose, such as rayon. It has been known for some time that ORC has haemostatic properties, and that application of ORC fabric can be used to reduce the extent of post-surgical adhesions in abdominal surgery.

The oxidized regenerated cellulose (ORC) can be obtained by the process described in U.S. Pat. No. 3,122,479. This material offers numerous advantages including the features that it is biocompatible, biodegradable, non-immunogenic and readily commercially available. ORC is available with varying degrees of oxidation and hence rates of degradation. The ORC may be used in the form of insoluble fibers, including woven, non-woven and knitted fabrics.

Chitin is a natural biopolymer composed of N-acetyl-D-glucosamine units. Chitin may be extracted from the outer shell of shrimps and crabs in known fashion. The chitin is then partially deacetylated, for example by treatment with 5M-15M NaOH, to produce chitosan. Complete deacetylation of the chitin is not a practical possibility, but preferably the chitosan is at least 50% deacetylated, more preferably at least 75% deacetylated. Chitosan has been employed for wound treatment in various physical forms, e.g. as a solution/gel; film/membrane; sponge; powder or fiber. Chitosan in the free base form is swellable but not substantially soluble in water at near-neutral pH, but soluble in acids due to the presence of ammonium groups on the chitosan chain. The solubility of the chitosan may be reduced by cross-linking, for example with epichlorhydrin. Typically, the average molecular weight of the chitosan as determined by gel permeation chromatography is from about $10^5$ to about $10^6$.

The collagen useful as the solid substrate on the materials according to the present invention may be any collagen, including Type I or Type II or Type III collagen, natural fibrous collagen, atelocollagen, partially hydrolysed collagens such as gelatin, and combinations thereof. Recombinant human collagen, for example as described in U.S. Pat. No. 5,962,648 and WO-A-2004078120 may be used. Natural fibrous collagen, for example of bovine origin, is suitable. For example, the collagen prepared from bovine hide is a combination of Type I collagen (85%) and Type III collagen (15%).

In certain embodiments of the present invention, the oxidized cellulose is complexed with collagen and/or chitosan to form structures of the kind described in WO98/00180, WO98/00446 or WO2004/026200. For example, the oxidized cellulose may be in the form of milled ORC fibres that have been dispersed in an aqueous suspension of collagen and then freeze-dried or solvent dried to form a bioabsorbable sponge. This provides for certain therapeutic and synergistic effects arising from the complexation with collagen, as described in the above-referenced patent specifications.

In particular embodiments, the polymeric substrate comprises (and may consist essentially of) a mixture of: (a) collagen and/or chitosan; and (b) oxidized regenerated cellulose, for example in a dry weight ratio range of from about 90:10 to about 10:90 of collagen/chitosan:ORC, preferably from about 75:25 to about 25:75, and particularly from about 60:40 to about 40:60.

The cell lysate or releasate is dispersed in and/or on the surface of the solid vehicle in a therapeutically effective concentration. That is to say, at a concentration that results in increased fibroblast proliferation relative to a control with no cell lysate or releasate, as determined by Procedure 1 below.

The solid wound healing compositions according to the present invention are suitably substantially dry. In certain embodiments, they may comprise up to about 20% by weight, preferably from about 2% to about 10% by weight of water. The solid compositions according to the present invention may also contain 0-40% by weight, for example from about 5 to about 25% by weight, of a plasticiser, preferably a polyhydric alcohol such as glycerol or sorbitol.

In certain embodiments, the wound healing compositions according to the present invention may also comprise up to about 10% by weight, for example from about 0.01 to about 5% by weight, typically from about 0.1 to about 2% by weight of one or more other wound healing therapeutic agents, such as non-steroidal anti-inflammatory drugs (e.g. acetaminophen), steroids, local anaesthetics, antimicrobial agents, or growth factors (e.g. fibroblast growth factor or platelet derived growth factor). The antimicrobial agent may, for example, comprise an antiseptic, an antibiotic, or mixtures thereof. Preferred antibiotics include tetracycline, penicillins, terramycins, erythromycin, bacitracin, neomycin, polymycin B, mupirocin, clindamycin and mixtures thereof. Preferred antiseptics include silver, including colloidal silver, silver salts including salts of one or more of the anionic polymers making up the material, silver sulfadiazine, chlorhexidine, povidone iodine, triclosan, sucralfate, quaternary ammonium salts and mixtures thereof. The preferred antimicrobial agent is silver. Preferably, the amount of silver (as silver ions and metallic silver) in the materials according to the present invention is from about 0.01 wt % to about 2 wt. %, more preferably from about 0.05 wt % to about 0.5 wt. %, and most preferably about 0.1 wt. % to about 0.3 wt. %. Lesser amounts of silver could give insufficient antimicrobial effect. Greater amounts of silver could give rise to antiproliferative effects on wound healing cells.

All of the above percentages are on a dry weight basis.

In a second aspect, the present invention provides a wound dressing comprising a wound dressing composition according to any preceding claim.

The wound dressing composition in the dressing according to the present invention is typically in sheet or layer form, for example having an area of from about 1 cm$^2$ to about 400 cm$^2$, in particular from about 2 cm$^2$ to about 100 cm$^2$. The basis weight of the sheet is typically from about 100 g/m$^2$ to about 5000 g/m$^2$, for example from about 400 g/m$^2$ to about 2000 g/m$^2$. The sheet of the composition according to the present invention forms an active layer of the dressing.

The said active layer in the dressings according to the invention would normally be the wound contacting layer in use, but in some embodiments it could be separated from the wound by a liquid-permeable top sheet. Preferably, the area of the active layer is from about 1 cm$^2$ to about 400 cm$^2$, more preferably from about 4 cm$^2$ to about 100 cm$^2$.

The wound dressing may consist essentially of the active layer of the composition according to the present invention, in which case the dressing would normally be used in conjunction with a suitable secondary dressing. In other embodiments, the wound dressing according to the invention further comprises a backing sheet extending over the active layer opposite to the wound facing side of the active layer. Preferably, the backing sheet is larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

Preferably, the backing sheet is substantially liquid-impermeable. The backing sheet is preferably semipermeable. That is to say, the backing sheet is preferably permeable to water vapour, but not permeable to liquid water or wound exudate. Preferably, the backing sheet is also microorganism-impermeable.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive layer (where present) should be moisture vapour transmitting and/or patterned to allow passage of water vapour therethrough. The adhesive layer is preferably a continuous moisture vapour transmitting, pressure-sensitive adhesive layer of the type conventionally used for island-type wound dressings. Polyurethane-based pressure sensitive adhesives are preferred.

The wound dressing according to the present invention may further comprise an absorbent layer between the active layer and the backing sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof.

A removable cover sheet may protect the wound-facing surface of the dressing. The cover sheet is normally formed from flexible thermoplastic material. Suitable materials include polyesters and polyolefins. Preferably, the adhesive-facing surface of the cover sheet is a release surface. That is to say a surface that is only weakly adherent to the active layer and the adhesive on the backing sheet to assist removal of the cover sheet. For example, the cover sheet may be formed from a non-adherent plastic such as a fluoropolymer, or it may be provided with a release coating such as a silicone or fluoropolymer release coating.

Preferably, the wound dressing of the present invention is sterile and packaged in a microorganism-impermeable container.

In a further aspect, the present invention provides a process for the production of a wound dressing composition comprising the steps of: lysing hepatocyte or macrophage cells to form a lysate, and dispersing the lysate in or on a pharmaceutically acceptable carrier. Preferably, the wound dressing composition obtainable by the process of the invention is a wound dressing composition according to the present invention as hereinbefore defined.

In certain embodiments, the concentration of protease inhibitors in the cells of the non-viable cell lysate or releasate is raised over the basal level before the step of lysis. This is achieved by culturing the hepatocyte or macrophage cells in the presence of an agent selected from the group consisting of cytokines, bacterial endotoxins and exotoxins, and mixtures thereof. A suitable bacterial toxin for this purpose is lipopolysaccharide derived from E. Coli.

In certain embodiments, the lysate or releasate is freeze-dried before the step of dispersing. The step of dispersing may be carried out by mixing or coating the substrate material with the cell lysate. In certain embodiments, the lysate or releasate is mixed with an aqueous dispersion containing components of the solid substrate, and the mixture is then freeze-dried or solvent dried to form a sponge containing the lysate or releasate.

In a further aspect, the present invention provides the use of a non-viable cell lysate or releasate derived from a hepatocyte cell, a macrophage cell, or mixtures thereof, for the preparation of a medicament for the treatment of a wound. Suitably, the medicament is a wound dressing composition or a wound dressing as hereinbefore defined.

Suitably, the wound is a chronic wound. The compositions of the invention are expected to be especially useful for the treatment of chronic wounds because chronic wounds are known to exhibit elevated endogenous protease levels, which contribute to the delayed healing of these wounds. Exemplary chronic wounds include venous ulcers, decubitis ulcers and diabetic ulcers.

In a further aspect, the present invention provides a method of treatment of a wound in a mammal, comprising the step of applying a wound dressing composition according to the invention to the wound. Suitably, the wound is a chronic wound such as a decubitis ulcer, a venous ulcer or a diabetic ulcer.

Preferably, the dressing is applied to the chronic wound for a period of at least 1-hour, more preferably at least 6 hours, and most preferably at least 12 hours. The treatment may be extended for several days or weeks, with dressing changes as appropriate.

It will be appreciated that alternative or preferred features or embodiments that are described above in relation to any one aspect of the invention may also be applicable in any other aspect of the invention.

Figure 2:
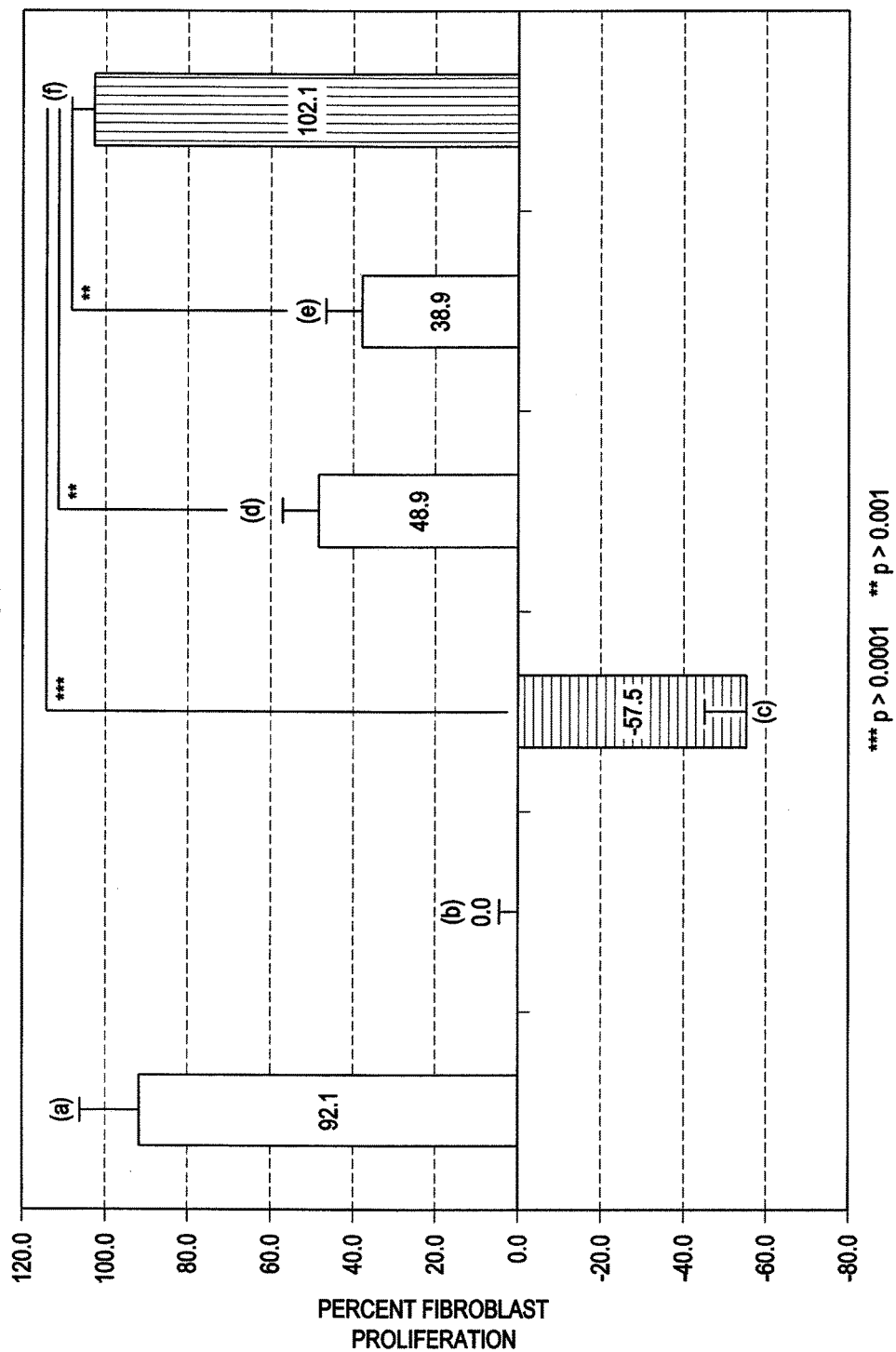
Figure 3:
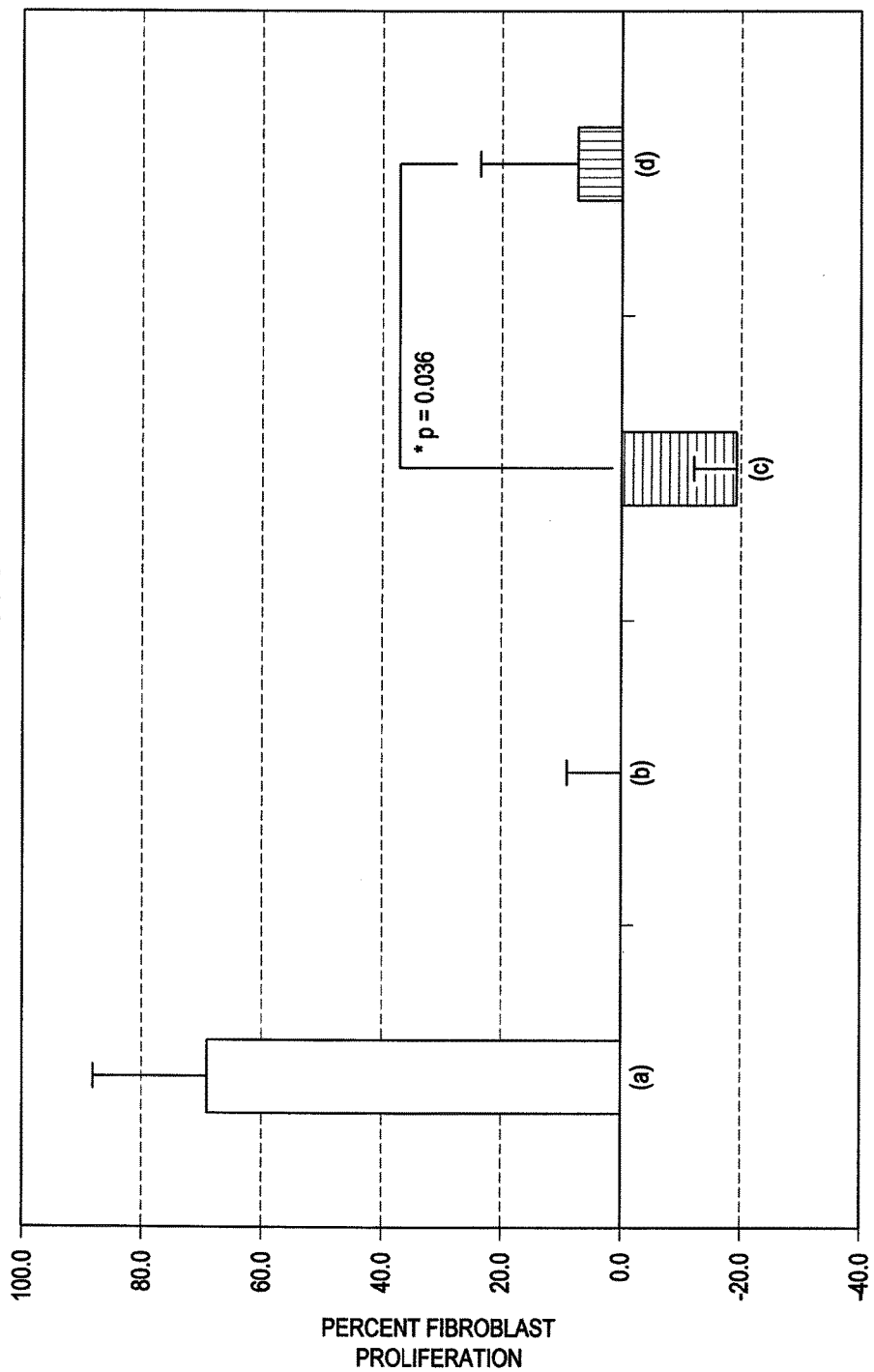

Various aspects and embodiments of the present invention will now be described in more detail by way of example, with reference to the accompanying drawings, in which:

FIG. 1 shows the percentage of cell stimulation of normal human dermal cells (fibroblasts) when incubated in the presence of chronic wound fluid (samples (a) and (b)) or acute wound fluid (sample (c));

FIG. 2 shows the percentage of fibroblast proliferation in dermal cell cultures incubated as follows (a) 10% serum as a positive control which stimulates cells; (b) serum free media as a negative control which maintains cells but gives no growth; (c) chronic wound fluid alone; (d) media (solution) in which the releasate was prepared; (e) both the chronic wound fluid and a monocyte cell releasate; and (f) both the chronic wound fluid and the macrophage releasate; and FIG. 3 shows the percentage of fibroblast proliferation in dermal cell cultures incubated as follows (a) 10% serum as a positive control which stimulates cells; (b) serum free media as a negative control which maintains cells but gives no growth; (c) chronic wound fluid alone; and (d) both the chronic wound fluid and a macrophage cell lysate.

EXAMPLE 1 & EXAMPLE 2

Macrophage cell releasates and lysates were prepared as follows.

Monocyte/macrophage cells (THP-1 cells) obtained from a commercial source were grown and maintained in cell culture media (RPMI 1640+2 mM Glutamine containing 10% FCS/FBS and 1% antibiotic/antimycotic). These cells are grown in suspension and are therefore routinely sub-cultured and used for experimental testing at a cell density of from 2 to $9 \times 10^5$ cells/ml. The cells were then harvested by centrifugation at 1000 rpm for 10 mins. The pellet is then re-suspended in RPMI media containing PMA (phorbol ester—Phorbol 12-myristate 13-acetate) to give a final concentration of $2.5 \times 10^{-7}$ M. This allows cells to become adherent and differentiated, i.e. to become macrophage-like. The cell suspension containing PMA was then used to seed three 24 well microtitre plates at a cell density of $8 \times 10^6$ cells/ml (i.e. 1 ml of cell suspension was added to each well). The plates were then incubated at 37° C., 5% $CO_2$ for 24 hours to allow adherence of cells to the tissue culture plastic.

The medium was then replaced by either RPMI+lipopolysaccharide (derived from E. Coli, at 10 ng/ml) or RPMI alone, and allowed to grow for 24 hours in a humidified incubator at 37° C., 5% $CO_2$. The added lipopolysaccharide stimulates the production of the desired cytokines, growth factors, proteases and protease inhibitors by the cells. The conditioned medium was then removed and labelled macrophage cell releasate. The remaining cell monolayer was harvested and suspended at a cell density of $1 \times 10^6$ cells/ml, after which they subjected to 3 freeze-thaw cycles in order to prepare a macrophage cell lysate.

EXAMPLE 3

Monocyte cell releasates were prepared as follows.

Monocyte/macrophage cells (THP-1 cells) obtained from a commercial source were grown and maintained in cell culture media (RPMI 1640+2 mM Glutamine containing 10% FCS/FBS and 1% antibiotic/antimycotic). These cells are grown in suspension and are therefore routinely sub-cultured and used for experimental testing at a cell density $2-9 \times 10^5$ cells/ml. The cells were then harvested by centrifugation at 1000 rpm for 10 mins. The pellet is then re-suspended in RPMI media and re-aliquoted at a cell density of $8 \times 10^6$ cells/ml. (i.e. 1 ml of cell suspension was added to each tube). Lipopolysaccharide toxin derived from E. Coli was added to some tubes (at 10 ng/ml in the RPMI medium) while others were left with RPMI medium alone; in all cases the cells were then incubated at 37° C., 5% $CO_2$ for 24 hours. The conditioned medium was then removed and labelled monocyte cell releasate.

Procedure 1

The expected effects of cell lysates and releasates on wound healing were studied in vitro as follows.

Incubating normal human dermal cells (fibroblasts) with chronic wound exudate (fluid) provides a model of a chronic wound. The ability of cell releasate or lysate to overcome the negative effect of the chronic wound environment and stimulate cell growth was assessed in order to determine whether cell releasate or lysate was able to stimulate healing in a chronic wound.

Adult human dermal fibroblasts isolated from a male donor (ATCC CRL-2068) were grown and maintained in Dulbecco's Modified Eagle's Medium (DMEM) containing 10% (v/v) foetal bovine serum (FBS). These cells were routinely sub-cultured and used for experimental testing when 95% confluent. Adult human dermal fibroblasts were then harvested and re-seeded in DMEM+10% FBS at a cell density of $4 \times 10^5$ cells/ml in a 96-well microtitre plate (100 μl/well). The cells were allowed to adhere and spread to the well surface for 24 hours in a humidified incubator at 37° C., 5% $CO_2$. The medium was then removed by aspiration and the cell monolayer washed with serum-free DMEM. Test samples were then added to the cell monolayer (100 μl/well), with at least 3 replicates of each material tested. All test samples were incubated with the cells for 72 hours at 37° C., 5% $CO_2$. After this incubation period a labelling solution was added from a commercial cell proliferation kit (XTT, Cell Proliferation kit II, Cat. No. 1 465 015, obtained from Boehringer Mannheim). An initial absorbance reading was obtained at 450 nm, and a final reading taken at 2.5 hrs, the microtiter plate was incubated at 37° C., 5% $CO_2$ during this time. The proliferative effect of each test condition was evaluated by comparing the absorbance readings measured. By using the positive (10% FBS/DMEM) and negative (Serum free DMEM) control values as 100% and 0% respectively all other conditions could be calculated as a % proliferation.

Test samples included acute and chronic wound fluid, obtained from patients with either a donor site wound or a chronic venous ulcer, respectively. The wound fluid was collected by aspiration in both cases.

Further experiments were carried out on a simulated wound fluid, which represents the hostile conditions of a chronic wound. The simulated wound fluid comprised PBS+ 2% BSA+elastase (5 ug/ml).

All wound fluids were diluted 1:2 with appropriate test samples, i.e. macrophage cell releasates, macrophage cell lysate, monocyte cell releasate, and incubated for 2 hours at 37° C. prior to addition to fibroblasts. At this point the test samples were further diluted 1:2 with serum free DMEM and added directly to the cell monolayer for evaluation in the cell proliferation assay as described above.

Referring to FIG. 1, it can be seen that the fibroblast proliferation for dermal cell samples (a) and (b) cultured in the chronic wound fluid was much lower, indeed negative, as compared to the cells (c) cultured in acute wound fluid. This is thought to be due to the presence of high levels of protease enzymes in the chronic wound fluid that degrade growth factors and otherwise interfere with cell proliferation.

Referring to FIG. 2, the dermal cells were incubated in (a) 10% serum as a positive control which stimulates cells; (b) serum free medium as a negative control which maintains cells but gives no growth; (c) chronic wound fluid alone; (d) the medium in which the releasate was prepared; (e) both the chronic wound fluid and a monocyte cell releasate; and (f) both the chronic wound fluid and the macrophage releasate.

The results show that the macrophage cell releasate significantly stimulates cell growth and can reverse the negative effect of the chronic wound environment. This effect is significantly better than the observed effect with the monocyte cell releasate.

Referring to FIG. 3, the samples are (a) 10% serum as a positive control which stimulates cells; (b) serum free medium as a negative control which maintains cells but gives no growth; (c) chronic wound fluid alone; and (d) both the chronic wound fluid and a macrophage cell lysate. It can be seen that the macrophage cell lysate sample (d) was also able to overcome the negative effect of the chronic wound environment and stimulate cell growth.

A similar effect would be achieved with hepatocytes. This is because macrophages and hepatocytes both produce a combination of growth factors and protease inhibitors, primarily alpha-1-antitrypsin.

The above embodiments have been described by way of example only. Many other embodiments falling within the scope of the accompanying claims will be apparent to the skilled reader.

The invention claimed is:

1. A wound dressing composition comprising a therapeutically effective concentration of a non-viable whole cell lysate or releasate of a macrophage that increases fibroblast proliferation compared to a control dressing composition that lacks the non-viable whole cell lysate or releasate, wherein the non-viable whole cell lysate or releasate comprises protease inhibitors that are secreted by the macrophage during its normal growth cycle.

2. The wound dressing composition according to claim 1, wherein the non-viable whole cell lysate or releasate is dispersed in or on a pharmaceutically acceptable vehicle.

3. The wound dressing composition according to claim 2, wherein the pharmaceutically acceptable vehicle is in the form of a solid sheet, a semi-solid ointment, an apertured solid sheet, a web, a woven fabric, a knitted fabric, a nonwoven fabric, a hydrophilic foam, a freeze-dried sponge or a solvent-dried sponge.

4. The wound dressing composition according to claim 3, wherein the pharmaceutically acceptable vehicle comprises a bioabsorbable freeze-dried sponge.

5. The wound dressing composition according to claim 1, wherein the non-viable whole cell releasate or lysate is dispersed in or on a solid vehicle that either comprises, or consists essentially of, a solid bioabsorbable material selected from the group consisting of collagen, chitosan, oxidized cellulose, or mixtures thereof.

6. The wound dressing composition according to claim 1 which is substantially dry.

7. The wound dressing composition according to claim 1, wherein the composition further comprises from about 0.01 to about 10% by weight on a dry weight basis of one or more wound healing therapeutic substances.

8. The wound dressing composition according to claim 1 which is substantially sterile.

9. The wound dressing composition according to claim 1, wherein the non-viable whole cell lysate or releasate increases fibroblast proliferation in a chronic wound environment.

10. A wound dressing composition comprising a non-viable whole cell lysate of a macrophage, the composition comprising a mixture of proteins, glycoproteins, polysaccharides, lipids and nucleic acids present intracellularly in the macrophage and secreted extracellularly from the macrophage.

11. The wound dressing composition according to claim 10, wherein the non-viable whole cell lysate is dispersed in or on a bioabsorbable freeze-dried sponge.

12. The wound dressing composition according to claim 10, wherein the non-viable whole cell lysate is dispersed in or on a pharmaceutically acceptable vehicle.

13. The wound dressing composition according to claim 12, wherein the pharmaceutically acceptable vehicle is in the form of a solid sheet, a semi-solid ointment, an apertured solid sheet, a web, a woven fabric, a knitted fabric, a nonwoven fabric, a hydrophilic foam, a freeze-dried sponge or a solvent-dried sponge.

14. The wound dressing composition according to claim 10, wherein the non-viable whole cell lysate is dispersed in or on a solid vehicle that either comprises, or consists essentially of, a solid bioabsorbable material selected from the group consisting of collagen, chitosan, oxidized cellulose, or mixtures thereof.

15. The wound dressing composition according to claim 10 which is substantially dry.

16. The wound dressing composition according to claim 10, wherein the wound dressing composition further comprises from about 0.01 to about 10% by weight on a dry weight basis of one or more wound healing therapeutic substances.

17. The wound dressing composition according to claim 10 which is substantially sterile.

* * * * *